United States Patent [19]

Setzer et al.

[11] Patent Number: 5,417,668
[45] Date of Patent: May 23, 1995

[54] REMOVABLE PROTECTIVE COVER FOR USE WITH A BODY CATHETER

[76] Inventors: Kathy P. Setzer; Deana L. Stump, both of 2270 John Byrd Rd., Morganton, N.C. 28655

[21] Appl. No.: 243,498
[22] Filed: May 16, 1994
[51] Int. Cl.⁶ .............................................. A61M 5/00
[52] U.S. Cl. .................................... 604/263; 128/878; 128/DIG. 6; 604/174
[58] Field of Search ............... 604/174, 179, 180, 263; 128/877, 878, 879, DIG. 6; 2/109, 111, 402, 408; 383/4

[56] References Cited

U.S. PATENT DOCUMENTS

| | | | |
|---|---|---|---|
| 1,096,477 | 5/1914 | Weisert | 2/402 |
| 1,439,649 | 12/1922 | Stein | 2/111 |
| 2,242,641 | 5/1941 | Berger | 2/111 |
| 2,431,571 | 11/1947 | Lehr | 2/402 |
| 3,678,516 | 7/1972 | Backer | 2/402 |
| 4,470,410 | 9/1984 | Elliott | 128/378 |
| 4,517,971 | 5/1985 | Sorbonne | 128/DIG. 6 |
| 4,591,356 | 5/1986 | Christie | 604/179 |
| 4,733,658 | 3/1988 | Ruthven, Jr. | 128/879 |
| 4,881,684 | 11/1989 | Chinman | 383/4 |
| 4,917,505 | 4/1990 | Bullard et al. | 383/4 |
| 4,935,011 | 6/1990 | Hogan | 604/263 |
| 4,976,698 | 12/1990 | Stokley | 128/DIG. 6 |
| 5,076,289 | 12/1991 | Darling | 128/DIG. 6 |
| 5,188,608 | 2/1993 | Fritts | 604/179 |

Primary Examiner—Paul J. Hirsch
Attorney, Agent, or Firm—W. Thad Adams, III

[57] ABSTRACT

The invention is a removable protective cover for enveloping a body catheter of a type having a first end for being inserted semi-permanently through the skin at an insertion site into the body of a patient, and a second end for extending outside of the body. The second end has at least one needle lumen for receiving a needle therein. The protective cover includes a sheet material, and complementary hook and loop fasteners carried by the sheet material for removably attaching the cover to the second end of the catheter. The sheet material is formed of a soft, nonirritating material for residing next to the skin of the patient. The sheet material is foldable around the second end of the catheter to define an inner, skin side segment and two opposed, outer flaps.

20 Claims, 9 Drawing Sheets

REMOVABLE PROTECTIVE COVER FOR USE WITH A BODY CATHETER

TECHNICAL FIELD AND BACKGROUND OF THE INVENTION

This invention relates to a removable protective cover for use with a body catheter. Body catheters are well known in the art, and are used as a method of gaining vascular access for medical treatment, such as dialysis. The catheter includes a first end for being inserted semi-permanently into a body insertion cite, and a second end for residing outside of the body. The second end of the catheter is generally attached to the body with an adhesive, and typically includes one or more needle lumens and end caps connected to the catheter for receiving a needle.

The cover of the present invention acts to comfortably shield the needle lumens and end caps of the catheter from the skin to provide a non-irritating barrier between these elements and the skin. The invention addresses the long felt need of individuals having a permanent or semi-permanent catheter connected to the body by providing a comfortable, protective cover to envelope the catheter, and thereby eliminate skin irritation caused by contact with the various elements of the catheter. The present invention is easily removed from the catheter, and provides for easy access to the needle-receiving end caps of the catheter during use.

SUMMARY OF THE INVENTION

Therefore, it is an object of the invention to provide a removable, protective cover for particular use with a body catheter.

It is another object of the invention to provide a protective cover which resides next to the skin of the patient to shield the skin from the various skin-irritating elements of the catheter.

It is another object of the invention to provide a protective cover which allows immediate and convenient access to the needle-receiving end caps of the catheter.

It is another object of the invention to provide a protective cover which is relatively inexpensive to manufacture.

It is another object of the invention to provide a protective cover which is disposable.

It is another object of the invention to provide a protective cover which is launderable, and reusable.

These and other objects of the present invention are achieved in the preferred embodiments disclosed below by providing a removable protective cover for enveloping a body catheter of a type having a first end for being inserted semi-permanently through the skin at an insertion site into the body of a patient, and a second end for extending outside of the body. The second end has at least one needle lumen for receiving a needle therein.

The protective cover includes a sheet material and cover attachment means. The sheet material is formed of a soft, non-irritating material for residing next to the skin of the patient. The sheet material is foldable around the needle lumen of the catheter to define an inner, skin side segment and two opposed, outer flaps. The cover attachment means is carried by the sheet material for removably attaching the cover to the needle lumen of the catheter.

According to one preferred embodiment of the invention, a releasable adhesive is carried by the inner skin side segment of the sheet material for releasably securing the cover to the skin of the patient.

According to another preferred embodiment of the invention, the cover attachment means includes releasable closure means for releasably closing the opposed, outer flaps of the sheet material together around the needle lumen of the catheter, and for permitting the cover to be removed by releasing the attachment of the opposed, outer flaps to each other.

According to yet another preferred embodiment of the invention, the releasable closure means are complementary hook and loop fasteners carried by the opposed, outer flaps of the sheet material.

According to yet another preferred embodiment of the invention, the opposed, outer flaps are positioned in overlying relation to each other when releasably closed together by the complementary hook and loop fasteners to envelope the needle lumen of the catheter.

According to yet another preferred embodiment of the invention, the cover attachment means is an adhesive strip applied to the sheet material.

According to yet another preferred embodiment of the invention, the sheet material includes an end tab for being folded upwardly and held in covering relation to a distal end of the needle lumen by engagement with the two opposed, outer flaps of the sheet material.

According to yet another preferred embodiment of the invention, the end tab includes releasable end tab attachment means for releasably securing the end tab in place in covering relation to the distal end of the needle lumen.

According to yet another preferred embodiment of the invention, the releasable end tab attachment means are complementary hook and loop fasteners carried by the end tab and a one of the first and second outer flaps of the sheet material.

According to yet another preferred embodiment of the invention, the sheet material is terry cloth.

According to yet another preferred embodiment of the invention, the sheet material is knitted fabric.

According to yet another preferred embodiment of the invention, the sheet material is a laminated disposable fabric having an inner moisture-impermeable layer and an outer, soft, nonwoven absorbent paper layer.

BRIEF DESCRIPTION OF THE DRAWINGS some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
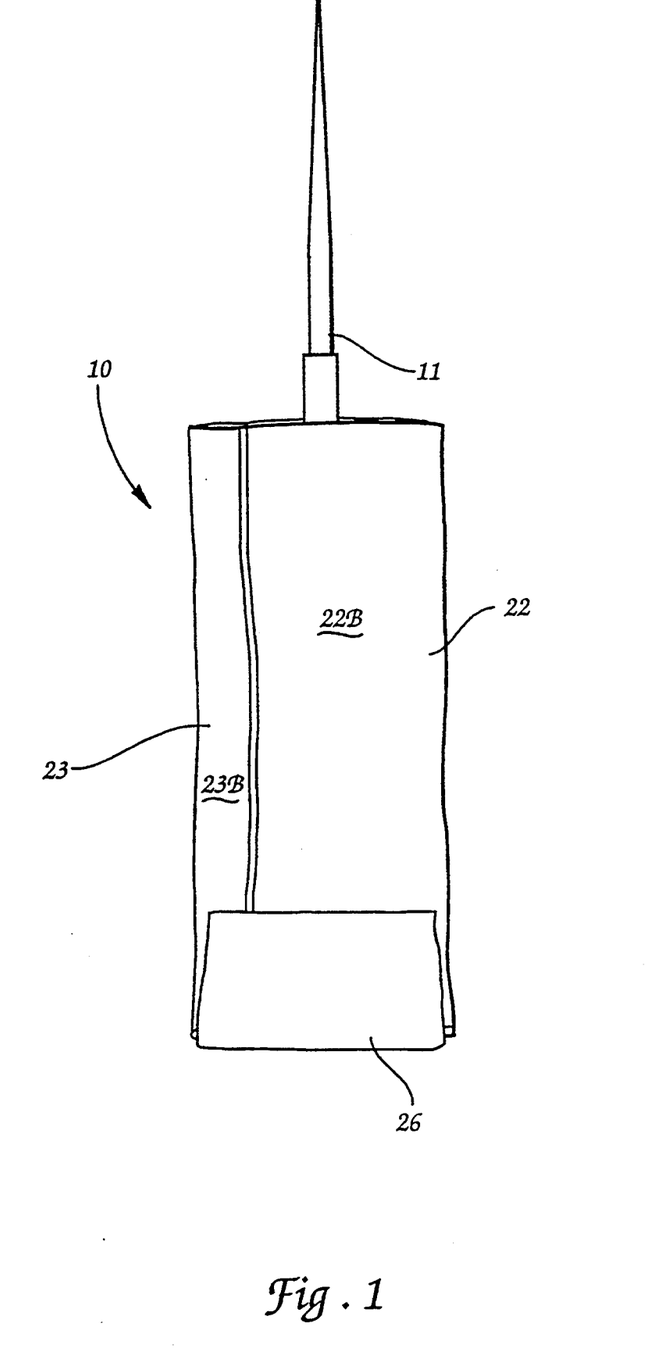
FIG. 1 is a front view of the cover according to one preferred embodiment of the invention, showing the cover folded around the catheter to shield the needle lumens, clamps, and end caps from the skin of the patient.

Referring now specifically to the drawings, a removable protective cover according to the present invention is illustrated in FIG. 1 and shown generally at reference numeral 10. The cover 10 is used for enveloping a portion of a body catheter 11 (See FIG. 2) having a first end 11A for being semi-permanently inserted through the skin at an insertion site into the body of a patient, and a second end 11B for extending outside of the body.

Figure 2:
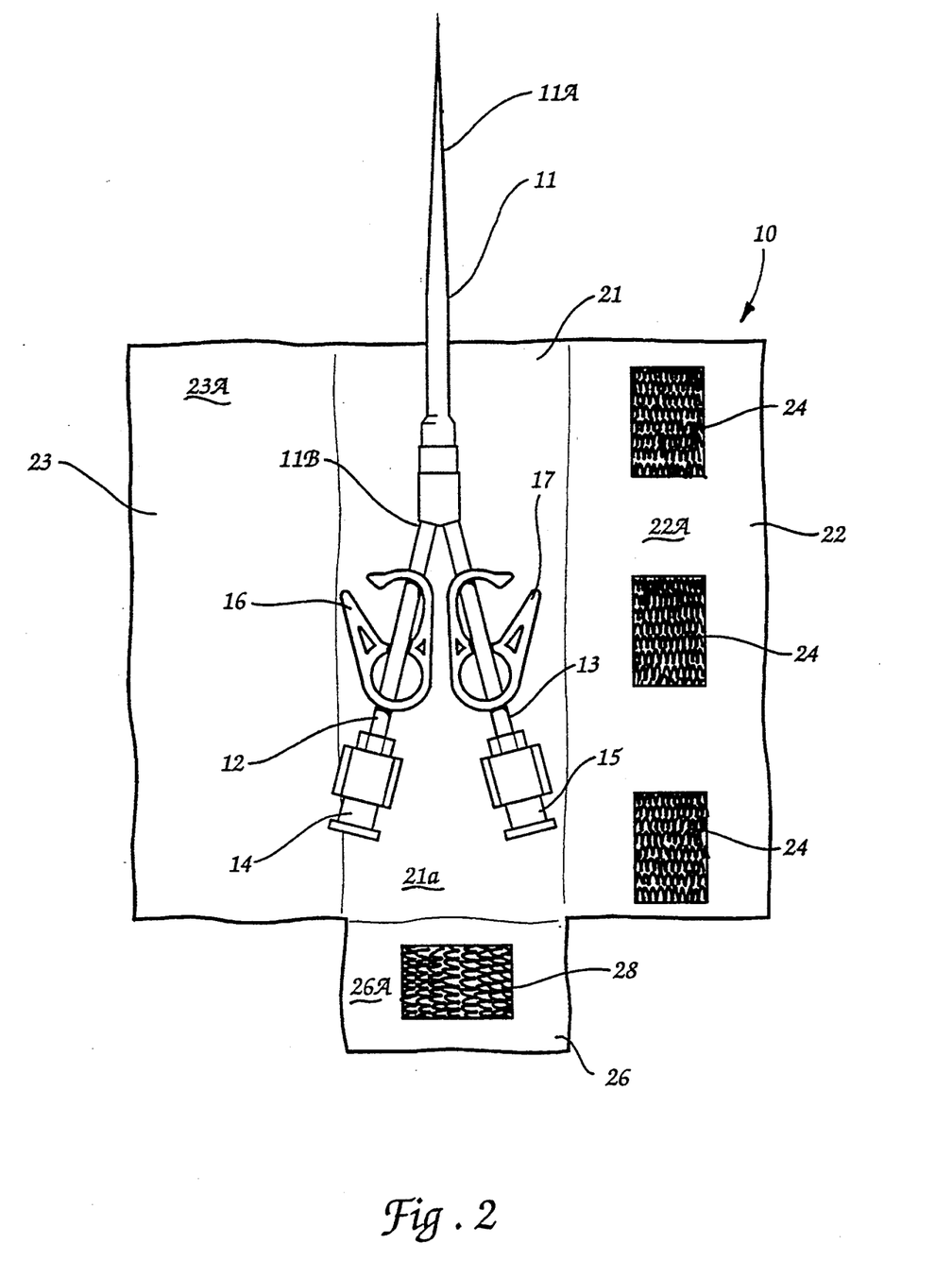
FIG. 2 is a front view of the cover unfolded, and showing the respective positions of the needle lumens, clamps, and end caps of the catheter within the cover.
Figure 7:
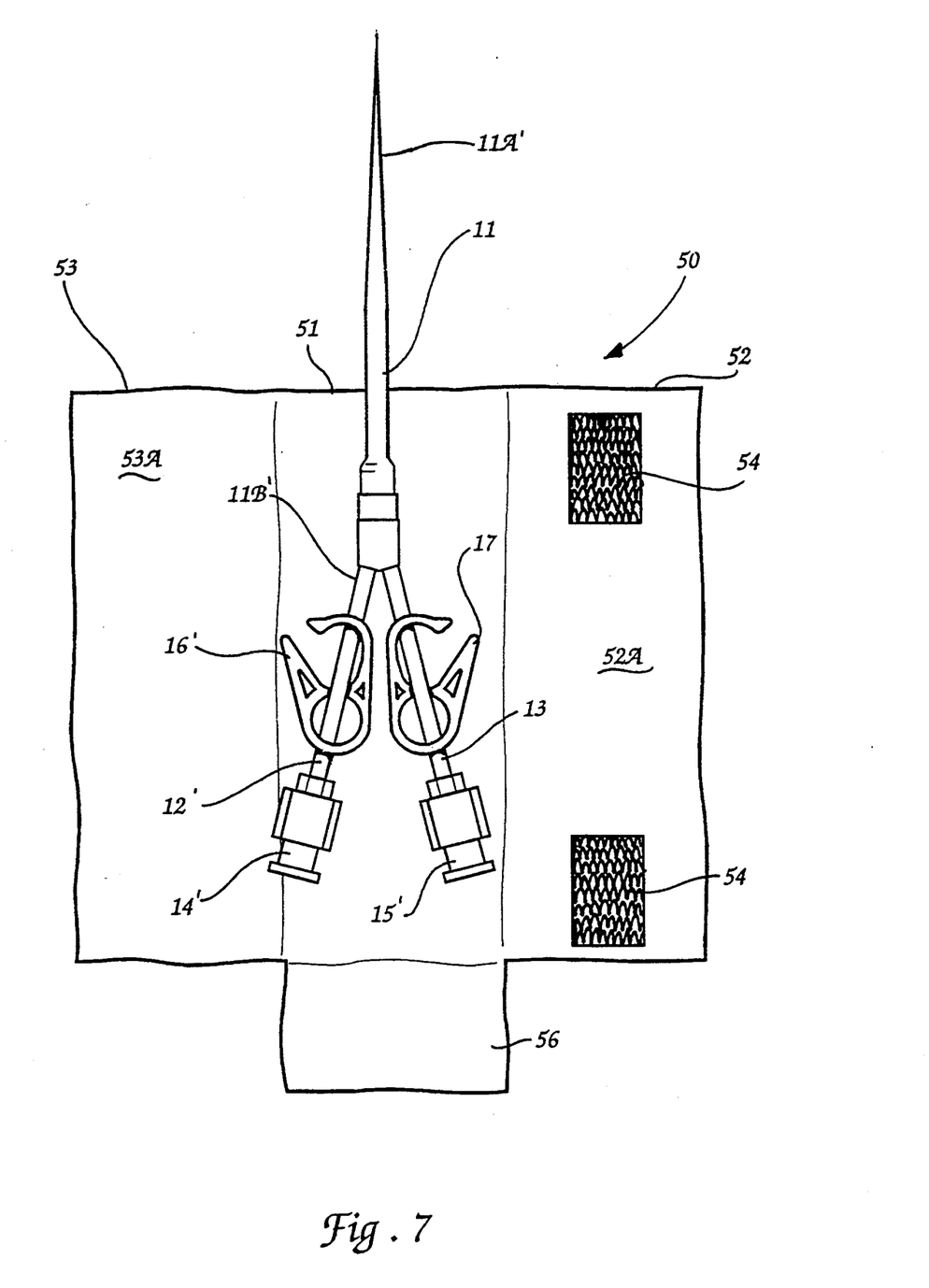
FIG. 7 is a front view of the cover according to a second embodiment of the invention, and illustrating the cover in an unfolded condition.

As best shown in FIGS. 2 and 7, the second end 11B of the catheter 11 includes separate needle lumens 12 and 13, such as arterial and venous lumens, and end caps 14 and 15 connected to each of the lumens 12 and 13 for receiving a needle for blood intake and blood return. The needle lumens 12 and 13 merge together with the body of the catheter 11, and preferably include respective clamps 16 and 17 which are color-coded to clearly identify each of the lumens 12 and 13. According to one preferred embodiment, the catheter 11 is of a type manufactured by Vas-Cath Incorporated, and sold under the trademark "Flexxicon."

The protective cover 10 envelopes the second end 11B of the catheter 11, including the needle lumens 12 and 13, clamps 16 and 17, and end caps 14 and 15, to shield these elements from the skin of the patient, and to provide a comfortable barrier between the catheter 11 and the skin. The cover 10 is preferably constructed of a soft, non-irritating sheet material, such as terry cloth, or a knit fabric material. Alternatively, the sheet material may be a laminated disposable fabric having an inner moisture-impermeable layer and an outer, soft, non-woven absorbent paper layer.

Figure 3:
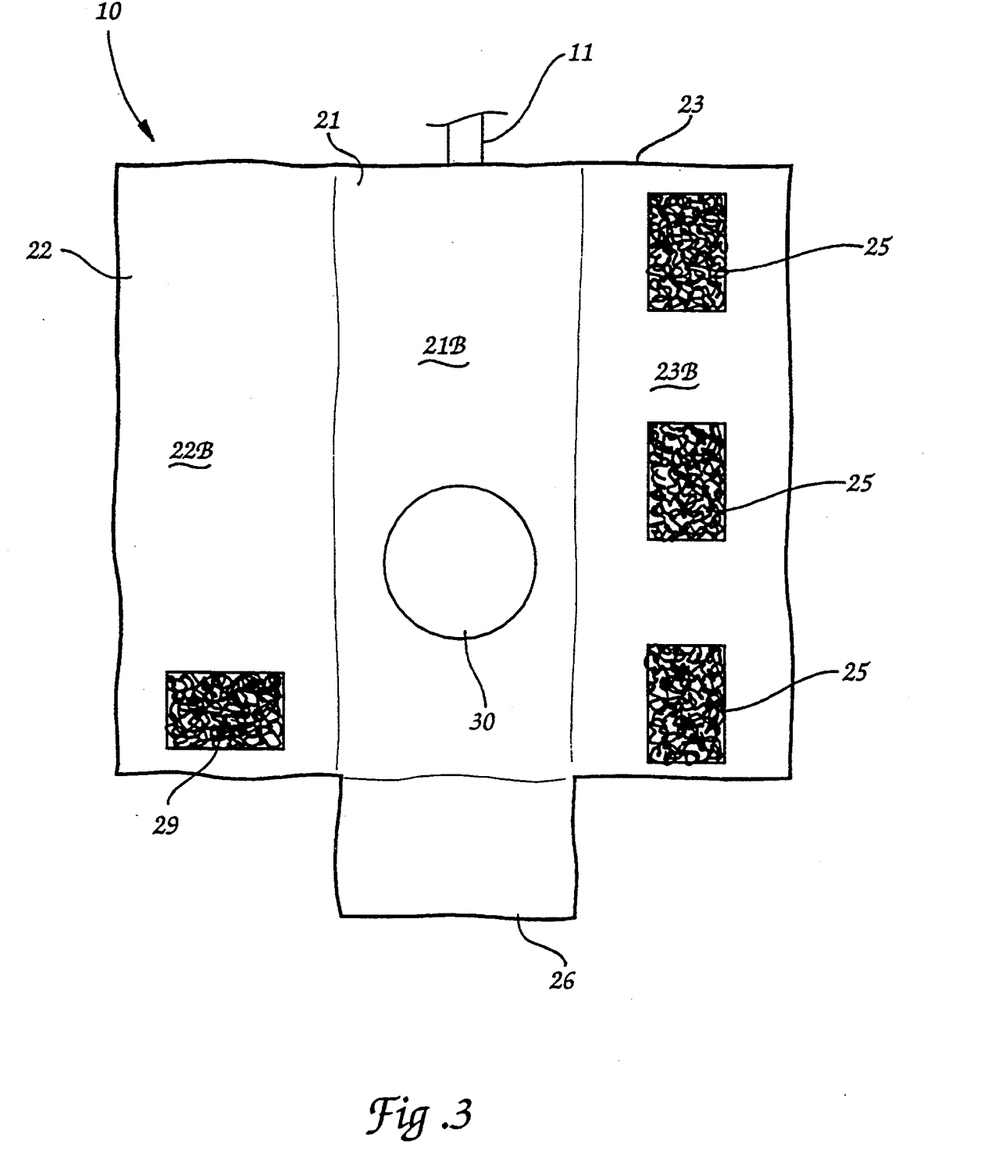
FIG. 3 is a back view of the unfolded cover shown in FIG. 2.

As best shown in FIGS. 2 and 3, the sheet material defines an inner, skin side segment 21 and two opposed, outer flaps 22 and 23. An inner surface 22A of the first outer flap 22 and an outer surface 23B of the second outer flap 23 preferably include complementary hook and loop fasteners 24 and 25 for releasably closing the outer flaps 22 and 23 together around the second end 11B of the catheter 11 and in overlying relation to each other. Alternatively, the outer flaps 22 and 23 may be closed together by an adhesive strip (not shown).

Preferably, the sheet material further includes an end tap 26 for being folded upwardly and held in covering relation to a distal end of the respective needle lumens 12 and 13. An inner surface 26A of the end tap 26 and an outer surface 22B of the first outer flap 22 may include complementary hook and loop fasteners 28 and 29 for releasably closing the open, distal end of the cover 10. Alternatively, the end tab 26 may be held to the outer surface 22B of the first outer flap 22 by an adhesive strip (not shown).

As shown in FIG. 3, an outer surface 21B of the inner segment 21 next to the skin preferably includes an adhesive patch 30. The patch 30 serves to removably attach the cover 10 and second end 11B of the catheter 11 to the body of the patient.

Figure 4:
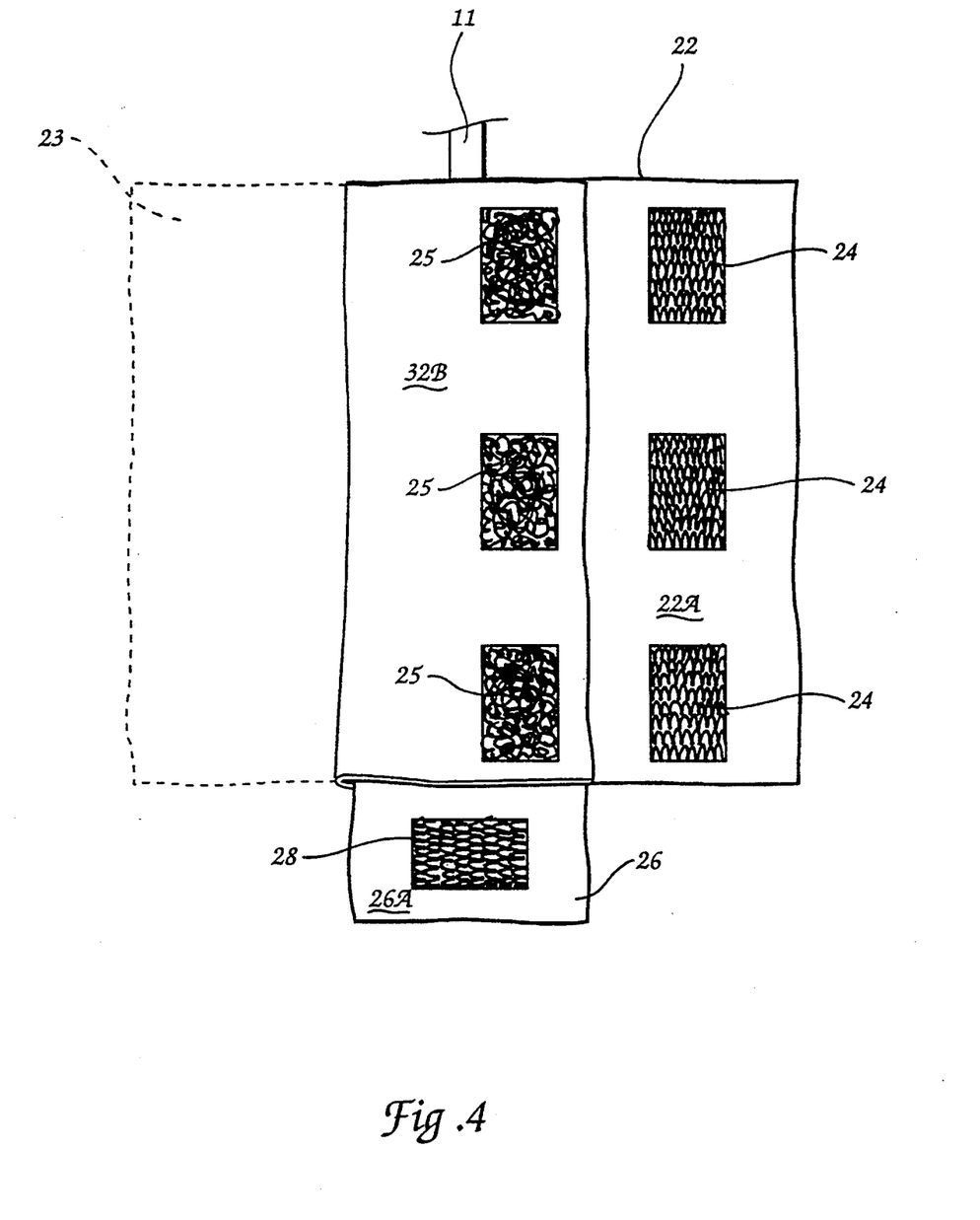
FIG. 4 is a front view of the cover showing the second outer flap folded over the needle lumens, clamps, and end caps of the catheter, and illustrating in phantom the position of the second outer flap prior to folding.
Figure 5:
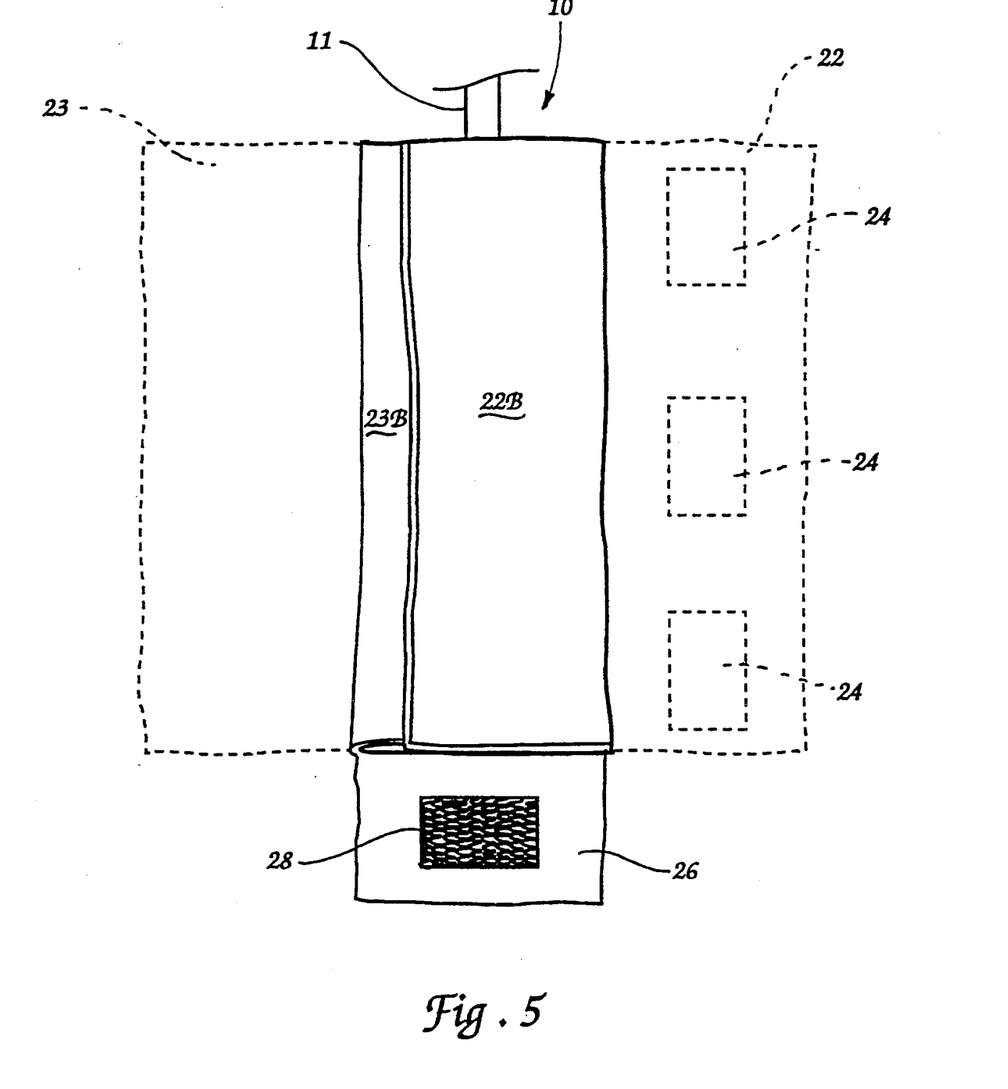
FIG. 5 is a front view of the cover showing the first and second outer flaps closed together in an overlying position, and illustrating in phantom the position of the first and second outer flaps prior to closing.
Figure 6:
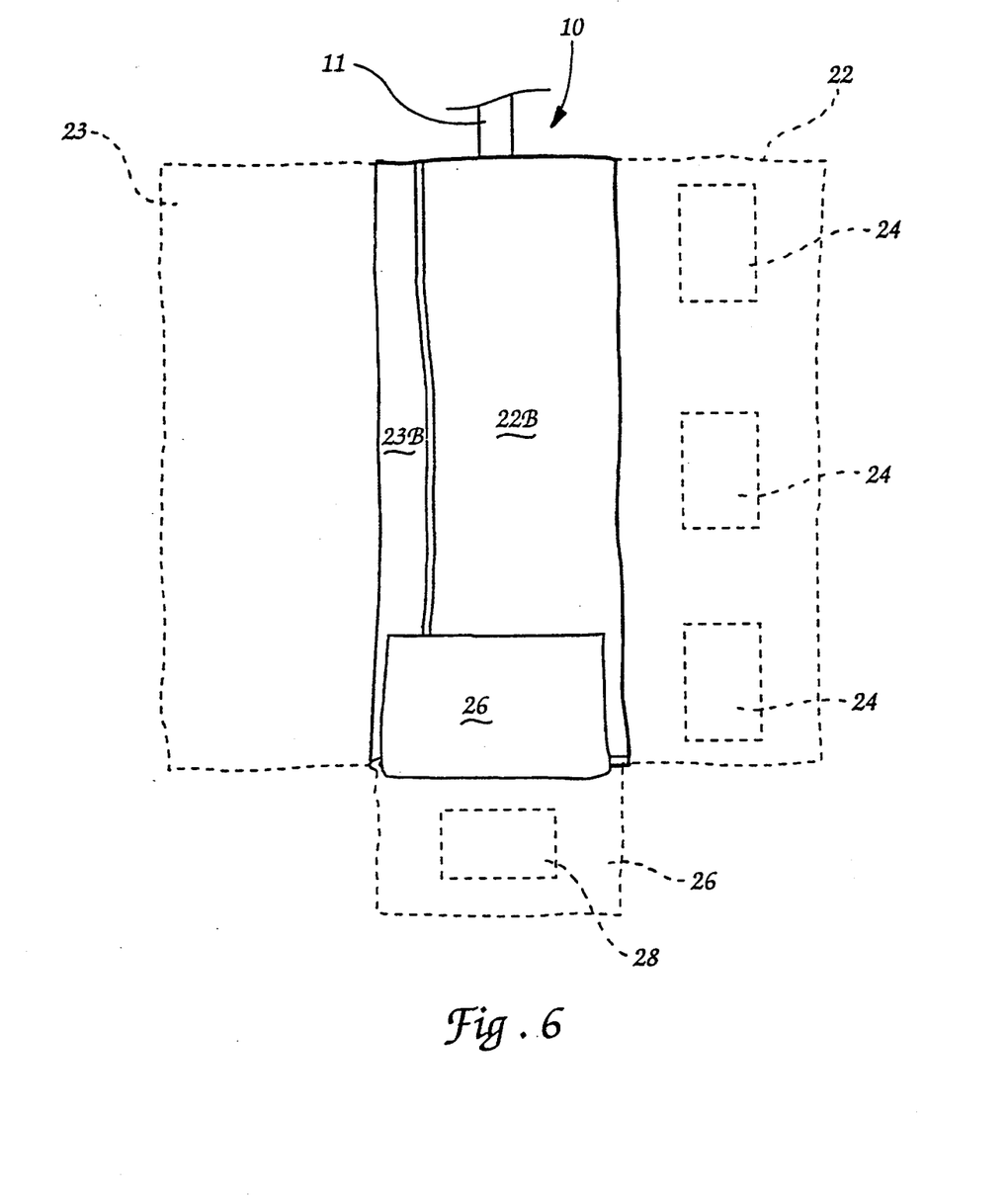
FIG. 6 is a front view of the cover folded around the needle lumens, clamps, and end caps of the catheter, and illustrating in phantom the position of the first and second outer flaps, and end tap prior to folding.

FIGS. 4-6 demonstrate the application of the cover 10 to the catheter 11. As shown in FIG. 4, the second outer flap 23 is first folded over the second end 11B of the catheter 11 to sandwich the needle lumens 12 and 13, clamps 16 and 17, and end caps 14 and 15 of the catheter 11 between the inner segment 21 and second outer flap 23 of the sheet material. The first outer flap 22 is then folded over the second outer flap 23, as shown in FIG. 5, and the complementary hook and loop fasteners 24 and 25 mated together to releasably close the flaps 22 and 23 in overlying relation to each other. Finally, the end tap 26 is folded upwardly to releasably close the open, distal end of the cover 10, as shown in FIG. 6.

Figure 8:
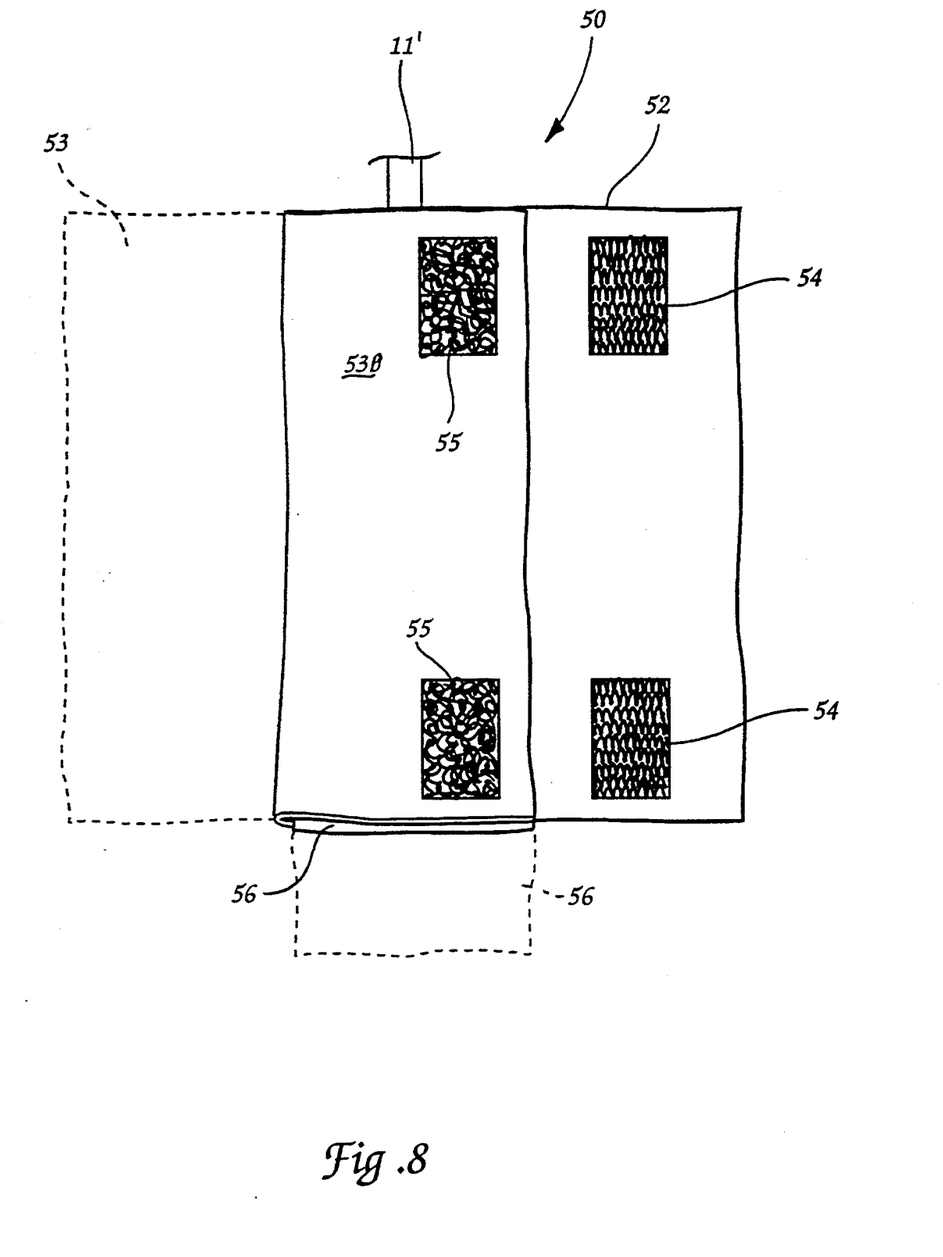
FIG. 8 is a front view of the cover illustrated in FIG. 7, showing the second outer flap folded over the needle lumens, clamps, and end caps of the catheter, and illustrating in phantom the position of the second outer flap prior to folding.
Figure 9:
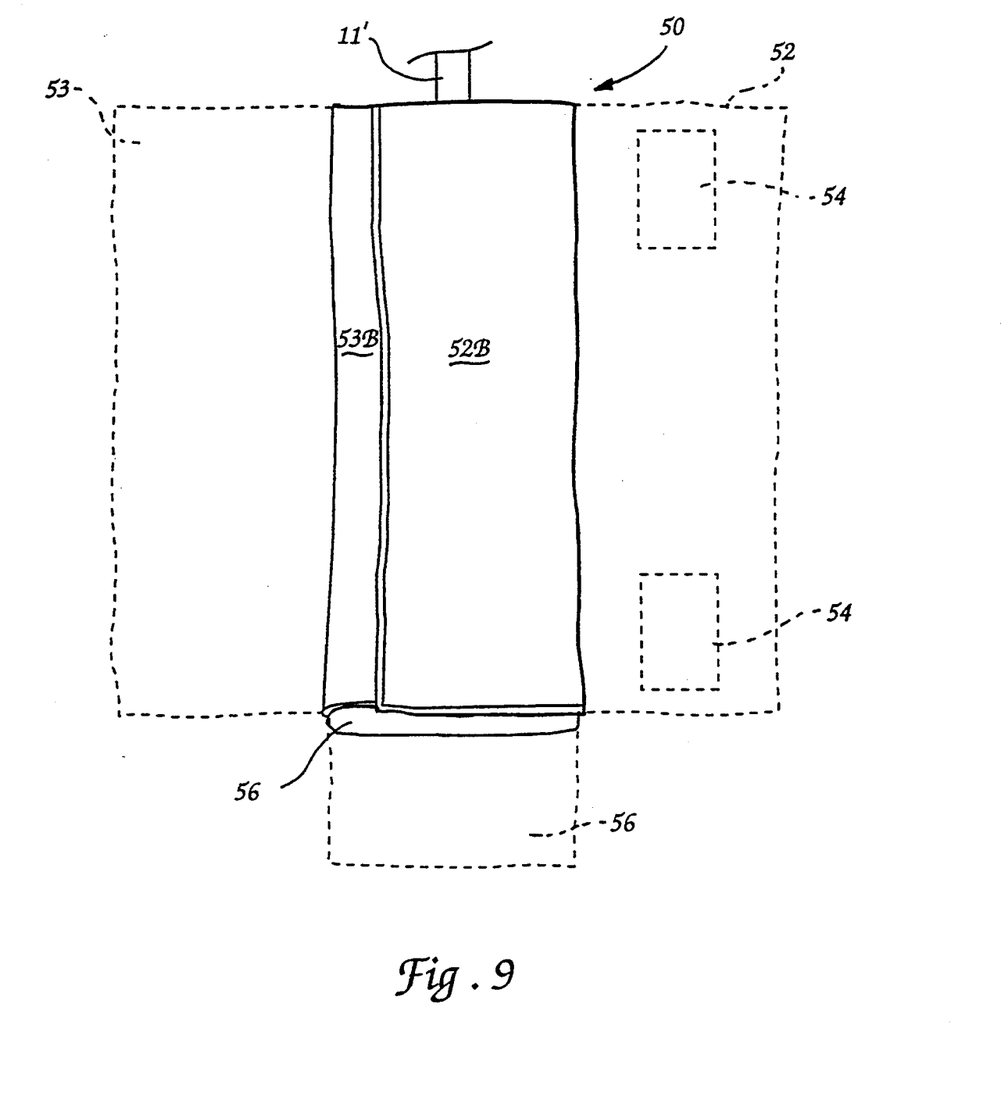
FIG. 9 is a front view of the cover illustrated in FIGS. 7, shown folded around the needle lumens, clamps, and end caps of the catheter, and illustrating in phantom the position of the first and second outer flaps, and end tap prior to folding.

A second preferred embodiment of the cover 50 is illustrated in FIGS. 7-9. The cover 50 is preferably used with a catheter 11' identical to that described above, and like elements are indicated in prime notation. In addition, the cover 50 includes a sheet material formed of a soft, non-irritating material identical to the material of the cover 10.

As best shown in FIG. 7, the sheet material defines an inner, skin side segment 51 and two opposed, outer flaps 52 and 53. An inner surface 52A of the first outer flap 52 and an outer surface 53B of the second outer flap 53 preferably include complementary hook and loop fasteners 54 and 55 for releasably closing the outer flaps 52 and 53 together around the second end 11B' of the catheter 11' and in overlying relation to each other. Alternatively, the outer flaps 52 and 53 may be closed together by an adhesive strip (not shown).

Preferably, the sheet material further includes an end tap 56 for being folded upwardly and held in covering relation to a distal end of the respective needle lumens 12' and 13'. The end tab 56 is held in place inside of the opposed outer flaps 52 and 53 of the sheet material by engagement with the outer flaps 52 and 53. Alternatively, the end tap 56 may be held in place by an adhesive strip (not shown).

Application of the cover 50 to the catheter 11' is illustrated in FIGS. 8 and 9. As shown in FIG. 8, the end tab 56 is first folded upwardly over the distal end of the respective needle lumens 12' and 13', and the second outer flap 53 folded over the second end 11B' of the catheter 11' to sandwich the needle lumens 12' and 13', clamps 16' and 17', and end caps 14' and 15' of the catheter 11' between the inner segment 51 and second outer flap 53 of the sheet material. The first outer flap 52 is then folded over the second outer flap 53, as shown in FIG. 9, and the complementary hook and loop fasteners 54 and 55 mated together to releasably close the flaps 52 and 53 in overlying relation to each other.

A removable protective cover is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. In combination with a body catheter of a type having a first end for being inserted semi-permanently through the skin at an insertion site into the body of a patient, and a second end for extending outside of the body, and having at least one needle lumen for receiving a needle therein, a removable protective cover enveloping the body catheter, said protective cover comprising:
   (a) a sheet material formed of a soft, non-irritating material for residing next to the skin of the patient, said sheet material being foldable around the second end of the catheter to define an inner, skin side segment and two opposed, outer flaps; and
   (b) cover attachment means carried by said sheet material for removably attaching the cover to the second end of the catheter.

2. A removable protective cover according to claim 1, wherein said cover attachment means comprises releasable closure means for releasably closing the opposed, outer flaps of the sheet material together around the needle lumen of the catheter, and for permitting the cover to be removed by releasing the attachment of the opposed, outer flaps to each other.

3. A removable protective cover according to claim 2, wherein said releasable closure means comprises complementary hook and loop fasteners carried by the opposed, outer flaps of the sheet material.

4. A removable protective cover according to claim 3, wherein the opposed, outer flaps are positioned in overlying relation to each other when closed together to envelope the needle lumen of the catheter.

5. A removable protective cover according to claim 1, wherein said cover attachment means comprising an adhesive strip applied to the sheet material.

6. A removable protective cover according to claim 1, wherein said sheet material includes an end tab for being folded upwardly and held in covering relation to a distal end of the needle lumen by engagement with the two opposed, outer flaps of the sheet material.

7. A removable protective cover according to claim 6, wherein said end tab includes releasable end tab attachment means for releasably securing said end tab in place in covering relation to the distal end of said needle lumen.

8. A removable protective cover according to claim 7, wherein said releasable end tab attachment means comprises complementary hook and loop fasteners carried by the end tab and a one of said first and second outer flaps of said sheet material.

9. A removable protective cover according to claim 1, wherein said sheet material comprises terry cloth.

10. A removable protective cover according to claim 1, wherein said sheet material comprises knitted fabric.

11. A removable protective cover according to claim 1, wherein said sheet material comprises a laminated disposable fabric having an inner moisture-impermeable layer and an outer, soft, nonwoven absorbent paper layer.

12. In combination with a body catheter of a type having a first end for being inserted semi-permanently through the skin at an insertion site into the body of a patient, and a second end for extending outside of the body, and having at least one needle lumen for receiving a needle therein, a removable protective cover for enveloping the body catheter, said protective cover comprising:
   (a) a sheet material formed of a soft, non-irritating material residing next to the skin of the patient, said sheet material being foldable around the second end of the catheter to define an inner, skin side segment and two opposed, outer flaps;
   (b) cover attachment means carried by said sheet material for removably attaching the cover to the second end of the catheter; and
   (c) a releasable adhesive carried by the inner skin side segment of the sheet material for releasably securing the cover to the skin of the patient.

13. A removable protective cover according to claim 12, wherein said cover attachment means comprises releasable closure means for releasably closing the opposed, outer flaps of the sheet material together around the needle lumen of the catheter, and for permitting the cover to be removed by releasing the attachment of the opposed, outer flaps to each other.

14. A removable protective cover according to claim 13, wherein said releasable closure means comprises complementary hook and loop fasteners carried by the opposed, outer flaps of the sheet material.

15. A removable protective cover according to claim 14, wherein the opposed, outer flaps of the sheet material are positioned in overlying relation to each other when closed together to envelope the needle lumen of the catheter.

16. A removable protective cover according to claim 12, wherein said cover attachment means comprises an adhesive applied to the sheet material.

17. A removable protective cover according to claim 12, wherein said sheet material includes an end tab for being folded upwardly and held in covering relation to a distal end of the needle lumen by engagement with the two opposed, outer flaps of the sheet material.

18. A removable protective cover according to claim 12, wherein said sheet material comprises terry cloth.

19. A removable protective cover according to claim 12, wherein said sheet material comprises knitted fabric.

20. A removable protective cover according to claim 12, wherein said sheet material comprises a laminated disposable fabric having an inner moisture-impermeable layer and an outer, soft, nonwoven absorbent paper layer.

* * * * *